United States Patent [19]
Ohnishi et al.

[11] Patent Number: 5,227,547
[45] Date of Patent: Jul. 13, 1993

[54] METHOD FOR PRODUCING DICHLOROPENTAFLUOROPROPANES

[75] Inventors: Keiichi Ohnishi; Hidekazu Okamoto; Toshihiro Tanuma, all of Yokohama; Koichi Yanase; Toru Kawasaki, both of Ichihara; Ryutaro Takei, Tokyo, all of Japan

[73] Assignee: Asahi Glass Company Ltd., Tokyo, Japan

[21] Appl. No.: 914,591

[22] Filed: Jul. 20, 1992

Related U.S. Application Data
[62] Division of Ser. No. 720,491, May 5, 1991.

[30] Foreign Application Priority Data
| Dec. 5, 1989 | [JP] | Japan | 1-314252 |
| Dec. 5, 1989 | [JP] | Japan | 1-314253 |
| Dec. 19, 1989 | [JP] | Japan | 1-327338 |
| Mar. 1, 1990 | [JP] | Japan | 2-47232 |
| Mar. 8, 1990 | [JP] | Japan | 2-54839 |
| Jul. 31, 1990 | [JP] | Japan | 2-201305 |

[51] Int. Cl.$^5$ .................. C07C 17/28; C07C 21/18
[52] U.S. Cl. ................................................ 570/172
[58] Field of Search .................................... 570/172

[56] References Cited
U.S. PATENT DOCUMENTS
| 2,449,360 | 9/1948 | Austin | 570/172 |
| 2,462,402 | 2/1949 | Joyce, Jr. et al. | |
| 3,795,710 | 3/1974 | Signeurin . | |

FOREIGN PATENT DOCUMENTS
| 0421322 | 4/1991 | European Pat. Off. | 570/172 |
| 261689 | 7/1913 | Fed. Rep. of Germany . | |
| 47-18086 | 5/1972 | Japan . | |
| 570470 | 7/1945 | United Kingdom . | |
| 581254 | 10/1946 | United Kingdom . | |
| 1010352 | 11/1965 | United Kingdom . | |

OTHER PUBLICATIONS
Freidel-Craft and Related Reaction, Ed. George A. Olah, Dow Chemical of Canada, Ltd, Ontario, Canada, (1963), pp. 26–29.

Collection of Czechoslovak Chemical Communications, vol. 36, 1971, (Prague, CST), O. Paleta et al.: "Addition reactions of haloolefins. XI. Reaction of tetrafluoroethylene with monofluoromethanes in the presence of aluminum chloride", pp. 1867–1875.

*Primary Examiner*—Werren B. Lone
*Attorney, Agent, or Firm*—Oblon, Spivak, McClelland, Maier & Neustadt

[57] ABSTRACT
A method for producing a dichloropentafluoropropane, which comprises reacting dichlorofluoromethane (R21) with tetrafluoroethylene (4F) in the presence of a Lewis acid catalyst for addition reaction to obtain dichloropentafluoropropane, wherein a halide containing at least one element selected from the group consisting of Sb, Nb, Ta, B, Ga, In, Zr, Hf and Ti, or AlBr$_3$, or AlI$_3$, is used as the Lewis acid.

3 Claims, No Drawings

METHOD FOR PRODUCING DICHLOROPENTAFLUOROPROPANES

This is a division of application Ser. No. 07/720,491, filed on Jul. 5, 1991.

DESCRIPTION

1. Technical Field

The present invention relates to a method for producing dichloropentafluoropropanes (R225s). Hydrochlorofluoropropanes are expected to be useful as foaming agents, cooling media or cleaning agents like conventional chlorofluorocarbons.

2. Background of the Invention

As a method for producing the dichloropentafluoropropanes (R225s), it is known to synthesize 3,3-dichloro-1,1,1,2,2-pentafluoropropane (R225ca) and 1,3-dichloro-1,1,2,2,3-pentafluoropropane (R225cb) as shown below by adding tetrafluoroethylene to dichlorofluoromethane in the presence of aluminum chloride:

$$CF_2=CF_2 + CHCl_2F \xrightarrow{AlCl_3} \begin{array}{c} CF_3CF_2CHCl_2 \\ + \\ CClF_2CF_2CHClF \end{array}$$

(O. Paleta et al., Collect, Czech. Chem. Commun., 36, 1867 (1971)). However, in this reaction, dichlorofluoromethane is disproportionated as shown by the following formula, $$CHCl_2F \xrightarrow[\text{disproportionation}]{AlCl_3} CHCl_3 + CHClF_2$$

and by-product chloroform (R20) which is hardly separable by a usual method such as distillation is formed in a large amount. Thus, this method has a disadvantage that a multi-step purification process is required to obtain a product in high purity.

SUMMARY OF THE INVENTION

The present inventors have conducted extensive researches on a method for efficiently producing dichloropentafluoropropanes (R225s) and as a result, have found it possible to obtain R225s in high yield by reacting tetrafluoroethylene with dichlorofluoromethane (R21) in the presence of a Lewis acid catalyst selected from the group consisting of a halide containing at least one element selected from the group consisting of Sb, Nb, Ta, B, Ga, In, Zr, Hf and Ti; AlBr$_3$; AlI$_3$; or a fluoride of the formula:

$$MX_\alpha F_\beta$$

wherein M is one of atoms selected from Group VIa, Group Va and Group IIIb, or a mixture of such atoms, X is one of Cl, Br and I atoms, or a mixture of such atoms, $\alpha$ is a real number of $0<\alpha<5$, and $\beta$ is a real number of $0<\beta\leq 3.5$ in the case of Group IVa, a real number of $0<\beta\leq 4.5$ in the case of Group Va and a real number of $0<\beta\leq 2.5$ in the case of Group IIIb, provided that $\alpha+\beta=$ an integer of from 3 to 5.

The halide containing at least one element selected from the group consisting of Sb, Nb, Ta, B, Ga, In, Zr, Hf and Ti includes chlorides such as SbCl$_5$, NbCl$_5$, TaCl$_5$, BCl$_3$, GaCl$_2$, GaCl$_3$, ZrCl$_4$, HfCl$_4$, InCl$_3$ and TiCl$_4$, and partially fluorinated compounds of such chlorides; fluorides such as SbF$_5$, NbF$_5$, TaF$_5$ and BF$_3$, and partially chlorinated compounds of such fluorides; bromides and iodides such as TaBr$_5$, AlBr$_3$, AlI$_3$, BBr$_3$, BI$_3$, GaBr$_3$, GaI$_3$, HfBr$_4$, HfI$_4$, InBr$_3$, InI$_3$ and TiBr$_4$, and partially chlorinated or fluorinated compounds of such bromides or iodides. The partially fluorinated chlorides and partially chlorinated fluorides include, for example, TiCl$_2$F$_2$, TiClF$_3$ and ZrCl$_2$F$_2$.

The fluoride of the formula MX$_\alpha$F$_\beta$ can readily be prepared by treating a halide of the formula:

$$MX_\alpha$$

wherein M is one of atoms selected from the group consisting of Group IVa, Group Va and Group IIIb, or a mixture of such atoms, X is one of Cl, Br and I atoms, or a mixture of such atoms, $\alpha$ is $\alpha=4$ in the case of Group IVa, $\alpha=5$ in the case of Group Va, and $\alpha=3$ in the case of Groups IIIb, for example, a chloride such as BCl$_3$, AlCl$_3$, GaCl$_3$, InCl$_3$, TiCl$_4$, ZrCl$_4$, HfCl$_4$, NbCl$_5$ or TaCl$_5$, or a bromide or iodide such as GaBr$_3$, GaI$_3$, InBr$_3$, InI$_3$, TaBr$_5$, AlBr$_3$, AlI$_3$, BBr$_3$, BI$_3$, TiBr$_4$, TiI$_4$, ZrBr$_4$, ZrI$_4$, HfBr$_4$, HfI$_4$, AlBr$_3$ or AlI$_3$, with a suitable fluorinating agent, for example, a chlorofluorocarbon (CFC) such as trichlorofluoromethane (R11), dichlorodifluoromethane (R12) or trichlorotrifluoromethane (R113), a hydrochlorofluorocarbon (HCFC) such as dichlorofluoromethane (R21) or chlorodifluoromethane (furon 22), hydrogen fluoride or fluorine gas.

The treating conditions vary depending upon the halide and the fluorine source. However, it is usual to employ at least an equimolar amount of the fluorine source to the halide.

The reaction temperature is usually from $-50°$ to $200°$ C., preferably from $-20°$ to $100°$ C., when chlorofluoromethane or hydrochlorofluoromethane is employed, and usually from $-20°$ to $200°$ C., preferably from $0°$ to $150°$ C., when other fluorine source such as hydrogen fluoride is employed.

The reaction time is usually from 10 minutes to 2 weeks, preferably from 1 hour to 1 day, when chlorofluoromethane or hydrochlorofluoromethane is employed, and usually from 30 minutes to two weeks, preferably from one hour to one day, when other fluorine source such as hydrogen fluoride is employed.

The content of fluorine atom contained in the fluoride of the formula MX$_\alpha$F$_\beta$ is preferably selected to be within a proper range in order to increase the yield of the dichloropentafluoropropanes while suppressing the production of chloroform. The range may vary depending upon the particle size when the fluoride is solid. However, it is usually $0<\beta\leq 3.5$, preferably $1<\beta\leq 3$, in the case of Group IVa, usually $0<\beta\leq 4.5$, preferably $1\leq\beta\leq 4$, in the case of Group Va, and usually $0<\beta\leq 2.5$, preferably $0.01\leq\beta\leq 2$, more preferably $0.1\leq\beta\leq 2$, in the case of Group IIIb.

The addition reaction of R21 to tetrafluoroethylene in the presence of a Lewis acid catalyst can be conducted in an inert solvent such as perfluorobutyltetrahydrofuran. However, in order to facilitate the purification, it is usually preferred to conduct the reaction in the absence of a solvent.

The amount of the catalyst varies depending upon the type of the catalyst used. However, it is usually from 0.01 to 50% by weight, preferably from 0.1 to 10% by weight, relative to the starting material. The reaction is conducted usually within a temperature range of from $-80°$ to $200°$ C., preferably from $-20°$ to $100°$ C. The reaction pressure is usually from 0 to 30 kg/cm².G, preferably from 0 to 15 kg/cm².G.

The amount of tetrafluoroethylene to be added is usually preferably at least equimolar to R21 to increase the conversion of R21.

If the addition reaction of R21 to tetrafluoroethylene (4F) in the presence of a Lewis acid catalyst is conducted under such reaction condition that the molar ratio of 4F to R21 is at least equimolar, preferably in an excess amount, the disproportionation reaction of R21 is substantially suppressed, whereby as shown by the following formula:

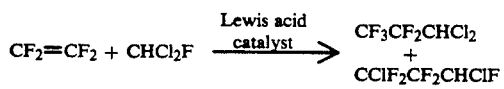

3,3-dichloro-1,1,1,2,2-pentafluoropropane (R225ca) and 1,3-dichloro-1,1,2,2,3-pentafluoropropane (R225cb) can be obtained in good yield, and chloroform produced in a small amount as a by-product by the disproportionation, will react with tetrafluoroethylene present in an excess amount to give 1,3,3-trichloro-1,1,2,2-tetrafluoropropane (R224ca) as shown by the following formula:

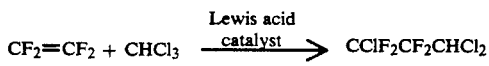

R224ca has a boiling point different from R225 and can easily be separated by distillation.

The amount of tetrafluoroethylene to be added is preferably at least equimolar to R21, although it may depend also on the amount of the Lewis acid. Preferably, the molar ratio of 4F to R21 is $1.01 \leq 4F/R21 \leq 10$, particularly $1.01 \leq 4F/R21 \leq 5$, more preferably $1.1 \leq 4F/R21 \leq 3$. The manner of supplying tetrafluoroethylene (4F) and dichlorofluoromethane (R21) is not particularly limited so long as the reaction condition is eventually such that 4F is present in an equimolar amount, preferably in an excess amount, to R21. However, in order to suppress the disproportionation reaction of R21, it is preferred to supply them continuously to the reactor while maintaining the molar ratio in supply of 4F to R21 within a range of $1 \leq 4F/R21$, preferably $1.01 \leq 4F/R21 \leq 10$, particularly $1.01 \leq 4F/R21 \leq 5$, more preferably $1.1 \leq 4F/R21 \leq 3$, and to withdraw the reaction product containing R225 from the reactor continuously. The excess amount of 4F can be recovered after the reaction. Therefore, 4F can be used in large excess at a level of 10 mol times or more, but it is not an economical operation.

The Lewis acid catalyst may be supplied preliminarily to the reactor, or it may be supplied continuously to the reactor together with 4F and R21 and withdrawn continuously from the reactor together with the reaction product. In the latter case, the recovered Lewis acid catalyst can be recycled.

If R21 remains in the reaction product, dispropornation takes place to form by-products such as chloroform. Therefore, in order to improve the selectivity for the desired reaction, it is always preferred to control the concentration of R21 to the minimum level. To minimize the concentration of R21 in the reactor, it is preferred to supply the starting materials R21 and 4F (and the catalyst) continuously to the reactor and to withdraw the reaction product continuously, so that the concentrations of the respective components can be maintained at constant levels, and if 4F is used in excess, it is possible to suppress the concentration of R21 to the minimum level. Thus, such an operation is preferred.

The reactor to be used for the continuous operation may be any so-called continuous reactor and may be of either continuous stirred tank reactor or plug flow reactor.

Further, it is necessary to feed solvent for the reaction at the initiation of the reaction. However, in the case of a continuous operation, as the reaction continuously proceeds, the solvent for reaction will gradually be replaced by the reaction product. Therefore, the solvent for reaction is not particularly restricted, so long as it does not adversely affect the main reaction.

As for the solvent at the initiation of the reaction, it is preferred to employ PFC such as perfluorooctane or perfluorobutyltetrahydrofuran, CFC such as 1,1,1-trichloropentafluoropropane (R215cb), 1,1,3-trichloropentafluoropropane (R215ca) or 1,1,1,3-tetrachlorotetrafluoropropane (R214cb), or HCFC such as 3,3-dichloro-1,1,1,2,2-pentafluoropropane (R225ca), 1,3-dichloro-1,1,2,2,3-pentafluoropropane (R225cb) or 1,3,3-trichloro-1,1,2,2-tetrafluoropropane (R224ca). However, it is possible to conduct the reaction without solvent. The reaction is conducted usually within a temperature range of from −80° to 200° C., preferably from −20° to 100° C. The reaction pressure is usually from 0 to 20 kg/cm², preferably from 0 to 10 kg/cm².

In the case of a continuous operation, the resident time of the reaction solution is usually from 0.1 minute to 24 hours, preferably from 1 minute to 10 hours, although it depends on the reaction temperatures and the type of the Lewis acid catalyst used.

The amount of the Lewis acid catalyst is usually from 0.1 to 50 mol%, preferably from 0.1 to 10 mol%, relative to R21. The catalyst to be used for this reaction is not particularly restricted so long as it is a Lewis acid. However, it is preferred to employ a halide containing at least one element selected from the group consisting of Al, Sb, Nb, Ta, B, Ga, In, Zr, Hf and Ti. For example, it is possible to employ chlorides such as $GaCl_2$, $GaCl_3$, $ZrCl_4$, $BCl_3$, $AlCl_3$, $HfCl_4$, $InCl_3$ and $TiCl_4$, or partially fluorinated compounds thereof, or bromides and iodides such as $GaBr_3$, $GaI_3$, $HfBr_4$, $HfI_4$, $InBr_3$, $InI_3$, and $TiBr_4$, or partially chlorinated or fluorinated compounds thereof, such as $TiCl_2F_2$, $TiClF_3$, and $ZrCl_2F_2$.

Further, chlorides such as $SbCl_5$, $NbCl_5$, $TaCl_5$, $BCl_3$ and partially fluorinated compounds thereof, fluorides such as $SbF_5$, $NbF_5$, $TaF_5$, and $BF_3$ are partially chlorinated compounds thereof, and bromides and iodides such as $TaBr_5$, $AlBr_3$, $BBR_3$ and $BI_3$ and partially chlorinated or fluorinated compounds thereof, may be used.

DESCRIPTION OF THE PREFERRED EMBODIMENT OF THE INVENTION

Now, the present invention will be described in further detail with reference to Examples. However, it should be understood that the present invention is by no means restricted by such specific Examples.

EXAMPLE 1

Into a 200 ml Hastelloy C autoclave, 2 g of antimony pentachloride was added and cooled to −78° C. Then, the autoclave was deaerated uner reduced pressure, and 155 g (1.5 mol) of R21 was added thereto. After charging 20 g of tetrafluoroethylene, the temperature was raised to 30° C., and tetrafluoroethylene was continuously added with stirring. Twelve hours later, the supply of tetrafluoroethylene was stopped, and stirring was continued for further 4 hours. The total amount of tetrafluoroethylene charged was 150 g. The pressure was returned to normal pressure, and then the reaction solution was washed with water, and about 220 g of the crude reaction product was recovered. The results of the analyses by means of gas chromatography and NMR are shown in Table 1.

TABLE 1

| Reaction product | Molar ratio (%) |
| --- | --- |
| R225 | 81 |
| Chloroform | 1 |
| Other components | 18 |

EXAMPLE 2

The reaction was conducted in the same manner as in Exampel 1 except that 2 g of niobium pentachloride was used instead of antimony pentachloride, whereby 190 g of the crude reaction product was recovered. The results of the analyses by means of gas chromatography and NMR are shown in Table 2.

TABLE 2

| Reaction product | Molar ratio (%) |
| --- | --- |
| R225 | 85 |
| Chloroform | 2 |
| Other components | 13 |

EXAMPLE 3

The reaction was conducted in the same manner in Example 1 except that 2 g of tantalum pentachloride was used instead of antimony pentachloride, whereby 190 g of the crude reaction product was recovered. The results of the analyses by means of gas chromatography and NMR are shown in Table 3.

TABLE 3

| Reaction product | Molar ratio (%) |
| --- | --- |
| R225 | 84 |
| Chloroform | 2 |
| Other components | 14 |

EXAMPLE 4

The reaction was conducted in the same manner as in Example 1 except that 2 g of aluminum bromide was used instead of antimony pentachloride and the reaction temperature was changed to $-10°$ C., whereby 240 g of the crude reaction product was recovered. The results of the analyses by means of gas chromatography and NMR are shown in Table 4.

TABLE 4

| Reaction product | Molar ratio (%) |
| --- | --- |
| R225 | 77 |
| Chloroform | 1 |
| Other components | 22 |

EXAMPLE 5

The reaction was conducted in the same manner as in Example 1 except that 2 g of aluminum iodide was used instead of antimony pentachloride and the reaction temperature was changed to $-10°$ C., whereby 240 g of the crude reaction product was recovered. The results of the analyses by means of gas chromatography and NMR are shown in Table 5.

TABLE 5

| Reaction product | Molar ratio (%) |
| --- | --- |
| R225 | 83 |
| Chloroform | 2 |
| Other components | 15 |

EXAMPLE 6

Into a 200 ml Hastelloy C autoclave, 2 g (0.009 mol) of zirconium(IV) chloride was added and cooled to $-78°$ C. Then, the autoclave was deaerated and 155 g (1.5 mol) of R21 was added thereto. After charging 20 g of tetrafluoroethylene, the temperature was raised to 10° C., and tetrafluoroethylene was continuously added while maintaining the reaction temperature within a range of from 10° to 20° C. Twelve hours later, the supply of tetrafluoroethylene was stopped, and stirring was continued for further 4 hours. The total amount of tetrafluoroethylene charged was 150 g. The pressure was returned to normal pressure, and then the reaction solution was washed with water, and 260 g of the crude reaction product was recovered. The results of the analyses by means of gas chromatography and NMR are shown in Table 6.

TABLE 6

| Reaction product | Molar ratio (%) |
| --- | --- |
| R225ca | 39 |
| R225cb | 42 |
| Chloroform | 1 |
| R224ca ($CClF_2CF_2CHCl_2$) | 15 |
| Other components | 3 |

EXAMPLE 7

The reaction was conducted in the same manner as in Example 6 except that 2 g of titanium tetrachloride was used instead of zirconium(IV) chloride, whereby 190 g of the crude reaction product was recovered. The results of the analyses by means of gas chromatography and NMR are shown in Table 7.

TABLE 7

| Reaction product | Molar ratio (%) |
| --- | --- |
| R225ca | 37 |
| R225cb | 43 |
| Chloroform | 5 |
| R224ca ($CClF_2CF_2CHCl_2$) | 10 |
| Other components | 5 |

EXAMPLE 8

The reaction was conducted in the same manner as in Example 6 except that 2 g of gallium trichloride was used instead of zirconium(IV) chloride, whereby 190 g of the crude reaction product was recovered. The results of the analyses by means of gas chromatography and NMR are shown in Table 8.

TABLE 8

| Reaction product | Molar ratio (%) |
| --- | --- |
| R225ca | 40 |
| R225cb | 30 |
| Chloroform | 3 |

TABLE 8-continued

| Reaction product | Molar ratio (%) |
| --- | --- |
| R224ca (CClF$_2$CF$_2$CHCl$_2$) | 16 |
| Other components | 11 |

EXAMPLE 9

The reaction was conducted in the same manner as in Example 6 except that 2 g of hafnium tetrachloride was used instead of zirconium(IV) chloride and the reaction temperature was changed to from 10° to 20° C., whereby 240 g of the crude reaction product was recovered. The results of the analyses by means of gas chromatography and NMR are shown in Table 9.

TABLE 9

| Reaction product | Molar ratio (%) |
| --- | --- |
| R225ca | 38 |
| R225cb | 41 |
| Chloroform | 2 |
| R224ca (CClF$_2$CF$_2$CHCl$_2$) | 11 |
| Other components | 8 |

EXAMPLE 10

The reaction was conducted in the same manner as in Example 6 except that 2 g of zirconium dichloride difluoride was used instead of zirconium(IV) chloride, whereby about 260 g of the crude reaction product was recovered. The results of the analyses by means of gas chromatography and NMR are shown in Table 10.

TABLE 10

| Reaction product | Molar ratio (%) |
| --- | --- |
| R225ca | 36 |
| R225cb | 54 |
| Chloroform | 1 |
| R224ca (CClF$_2$CF$_2$CHCl$_2$) | 6 |
| Other components | 3 |

EXAMPLE 11

The reaction was conducted in the same manner as in Example 6 except that 2 g of titanium dichloride difluoride was used instead of zirconium(IV) chloride, whereby about 260 g of the crude reaction product was recovered. The results of the analyses by means of gas chromatography and NMR are shown in Table 11.

TABLE 11

| Reaction product | Molar ratio (%) |
| --- | --- |
| R225ca | 37 |
| R225cb | 53 |
| Chloroform | 1 |
| R224ca (CClF$_2$CF$_2$CHCl$_2$) | 7 |
| Other components | 2 |

COMPARATIVE EXAMPLE 1-I

Into a 200 ml Hastelloy C autoclave, 3 g (0.02 mol) of anhydrous aluminum chloride was added and cooled to −78° C. Then, the autoclave was deaerated, and 155 g (1.5 mol) of R21 was added thereto. The temperature was raised to 10° C., and tetrafluoroethylene was continuously added while maintaining the reaction temperature within a range of from 10° to 20° C. Twelve hours later, the supply of tetrafluoroethylene was stopped, and stirring was continued for further 4 hours. The total amount of tetrafluoroethylene charged was 120 g. The pressure was returned to normal pressure, and then the reaction solution was washed with water, and about 200 g of the crude reaction product was recovered. The results of the analyses by means of gas chromatography and NMR are shown in Table 1-I.

TABLE 1-I

| Reaction product | Molar ratio (%) |
| --- | --- |
| R225ca | 27 |
| R225cb | 18 |
| Chloroform | 20 |
| R224ca (CClF$_2$CF$_2$CHCl$_2$) | 10 |
| Other components | 25 |

PREPARATION EXAMPLE 1

Into a 2 l three necked round bottom flask equipped with a reflux condenser, 200 g (1.5 mol) of anhydrous aluminum chloride and 2000 g (14.6 mol) of trichlorofluoromethane (R11) were charged under a nitrogen stream and generally stirred at 0° C. for 12 hours. After leaving the reaction mixture to stand still for 1 hour, the supernatant was removed, followed by drying under reduced pressure to obtain AlCl$_{3-\beta}$F$_\beta$. The fluorine content $\beta$ of this product was 0.1.

PREPARATION EXAMPLE 2

Into a 2 l three necked and round bottom flask equipped with a reflux condenser, 200 g (0.86 mol) of anhydrous zirconium(IV) chloride and 200 g (14.6 mol) of trichlorofluoromethane (R11) were charged under a nitrogen stream and stirred at 0° C. for 2 hours. After leaving the mixture to stand still for 1 hour, the supernatant was removed, followed by drying under reduced pressure to obtain ZrCl$_{4-\beta}$F$_\beta$. The fluorine content $\beta$ of this product was 1.6.

PREPARATION EXAMPLE 3

Into a 2 l three necked round bottom flask equipped with a reflux condenser, 200 g (1.1 mol) of anhydrous titanium tetrachloride and 2000 g (19.4 mol) of dichlorofluoromethane (R21) were charged under a nitrogen stream and stirred at 0° C. for 12 hours. After leaving the mixture to stand still for 1 hour, the supernatant was removed, followed by drying under reduced pressure to obtain TiCl$_{4-\beta}$F$_\beta$. The fluorine content $\beta$ of this product was 2.3.

PREPARATION EXAMPLE 4

Into a 1 l Hastelloy C autoclave, 200 g (0,6 mol) of anhydrous tantalum pentachloride was charged, and the autoclave was deaerated under reduced pressure. Then, 500 g (25 mol) of anhydrous hydrogen fluoride was added thereto, and the mixture was stirred at 50° C. for 5 hours. Then, hydrogen fluoride and hydrogen chloride were removed under reduced pressure to obtain TaCl$_{5-\beta}$F$_\beta$. The fluorine content $\beta$ of this product was 4.

EXAMPLE 12

Into a 10 l Hastelloy C autoclave, 0.1 kg of aluminum fluoride chloride prepared in Preparation Example 1 was charged, and the autoclave was deaerated under reduced pressure. Then, 3 kg (14. 8 mol) of R225ca ($CF_3CF_2CHCl_2$) was added thereto. The autoclave was cooled to $-10°$ C. Then, while maintaining the reaction temperature within a range of from 0° to 5° C., tetrafluoroethylene and R21 were continuously added at the rates of 850 g/hr and 670 g/hr, respectively. Six hours later, the supply of tetrafluoroethylene and R21 was stopped, and stirring was continued for further 4 hours while maintaining the reaction temperature within a range of from 5° to 10° C. The pressure was returned to normal pressure, and then the reaction solution was subjected to filtration, whereby about 10.7 kg of the crude reaction product was recovered. The results of the analyses by means of gas chromatography and $^{19}F$-NMR are shown in Table 12. The crude reaction product was purified by distillation to obtained 9.8 kg of R225 (dichloropentafluoropropane).

TABLE 12

| Composition of the reaction solution | Molar ratio (%) |
|---|---|
| R225ca ($CF_3CF_2CHCl_2$) | 71.5 |
| R225cb ($CClF_2CF_2CHClF$) | 23 |
| Chloroform ($CHCl_3$) | 0 |
| R224ca ($CClF_2CF_2CHCl_2$) | 2 |
| Other components | 3.5 |

EXAMPLE 13

The reaction was conducted in the same manner as in Preparation Example 1 except that 200 g (19.4 mol) of dichlorofluoromethane (R21) was used instead of trichlorofluoromethane (R11), to obtain aluminum fluoride chloride ($\beta$: 0.01). Then, using 0.1 kg of this product, the reaction was conducted in the same manner as in Example 12, whereby 10.8 kg of the crude reaction product was recovered. The results of the analyses by means of gas chromatography and NMR are shown in Table 13. The crude reaction product was purified by distillation to obtain 9.6 kg of R225 (dichloropentafluoropropane).

EXAMPLE 14

The reaction was conducted in the same manner as in Example 12 except that 0.1 kg of zirconium fluoride chloride obtained in Preparation Example 2 was used, whereby 10.8 kg of the crude reaction product was recovered. The results of the analyses by means of gas chromatography and NMR are shown in Table 13. The reaction product was purified by distillation to obtain 10.2 kg of R225 (dichloropentafluoropropane).

EXAMPLE 15

The reaction was conducted in the same manner as in Preparation Example 2 except that 2000 g (19.4 mol) of dichlorofluoromethane (R21) was used instead of trichlorofluoromethane (R11), whereby zirconium fluoride chloride was prepared ($\beta$:1.8). Then, using 0.1 kg of this product, the reaction was conducted in the same manner as in Example 12, whereby 10.7 kg of the crude reaction product was recovered. The results of the analyses by means of gas chromatography and NMR are shown in Table 13. The crude reaction product was purified by distillation to obtain 10.1 kg of R225 (dichloropentafluoropropane).

EXAMPLE 16

The reaction was conducted in the same manner as in Example 12 except that 0.2 kg of tantalum fluoride chloride prepared in Preparation Example 4 was used, whereby 9.5 kg of the crude reaction product was recovered. The results of the analyses by means of gas chromatography and NMR are shown in Table 13. The crude reaction product was purified by distillation to obtain 8.5 kg of R225 (dichloropentafluoropropane).

TABLE 13

| Composition of the reaction products (%) | Example Nos. | | | |
|---|---|---|---|---|
| | 13 | 14 | 15 | 16 |
| R225ca | 72 | 58 | 58 | 65 |
| R225cb | 22 | 40 | 41 | 23 |
| Chloroform | 0 | 0 | 0 | 1 |
| R224ca | 2 | 1.5 | 0.5 | 6.5 |
| Others | 4 | 0.5 | 0.5 | 4.5 |

EXAMPLE 17

The reaction was conducted in the same manner as in Example 12 except that 0.1 kg of titanium fluoride chloride prepared in Preparation Example 3 was used, whereby 10.5 kg of the crude reaction product was recovered. The results of the analyses by means of gas chromatography and NMR are shown in Table 14. The crude reaction product was purified by distillation to obtain 9.5 kg of R225 (dichloropentafluoropropane).

EXAMPLE 18

The reaction was conducted in the same manner as in Preparation Example 3 except that 2000 g (14.6 mol) of trichlorofluoromethane (R11) was used instead of dichlorofluoromethane (R21) and stirring was conducted at 10° C. for one week, whereby titanium fluoride chloride was prepared ($\beta$:2.2). Then, using 0.1 kg of this product, the reaction was conducted in the same manner as in Example 12, whereby 10.7 kg of the crude reaction product was recovered. The results of the analyses by means of gas chromatography and NMR are shown in Table 14. The crude reaction product was purified by distillation to obtain 9.6 kg of R225 (dichloropentafluoropropane).

EXAMPLE 19

The reaction was conducted in the same manner as in Preparation Example 1 except that 200 g of hafnium tetrachloride was used instead of zirconium(IV) chloride, whereby hafnium fluoride chloride ($\beta$:1,5) was prepared. Then, using 0.1 kg of this product, the reaction was conducted in the same manner as in Example 12, whereby 10.7 kg of the crude reaction product was recovered. The results of the analyses by means of gas chromatography and NMR are shown in Table 14. The crude reaction product was purified by distillation to obtain 9.9 kg of R225 (dichloropentafluoropropane).

EXAMPLE 20

The reaction was conducted in the same manner as in Preparation Example 2 except that 200 g of hafnium tetrachloride was used instead of zirconium(IV) chloride, 2000 g (19.4 mol) of dichlorofluoromethane (R21) was used instead of trichlorofluoromethane (R11), whereby hafnium fluoride chloride ($\beta$:1.7) was prepared. Then, using 0.1 kg of this product, the reaction was conducted in the same manner as in Example 12, whereby 10.6 kg of the crude reaction product was recovered. The results of the analyses by means of gas chromatography and NMR are shown in Table 14. The crude reaction product was purified by distillation to obtain 9.8 kg of R225 (dichloropentafluoropropane).

TABLE 14

| Composition of the reaction solution (%) | Example Nos. | | | |
|---|---|---|---|---|
| | 17 | 18 | 19 | 20 |
| R225ca | 60 | 61 | 60 | 59 |
| R225cb | 37 | 36 | 38 | 39 |
| Chloroform | 0 | 0 | 0 | 0 |
| R224ca | 2.5 | 2.5 | 1.5 | 1.5 |
| Others | 0.5 | 0.5 | 0.5 | 0.5 |

EXAMPLE 21

A 10 l Hastelloy C autoclave was deaerated under reduced pressure after 100 g of aluminum fluoride chloride prepared in Preparation Example 1 was charged. And then, 10 kg of 1,1,1-trichloropentafluoropropane (R215cb) was charged as an initial solvent. The autoclave was cooled to −10° C. Then, while maintaining the reaction temperature within a range of from 0° to 5° C., tetrafluoroethylene, dichlorofluoromethane and the aluminum fluoride chloride prepared in Preparation Example 1 were continuously added at the rate of 1300 g/hr, 1030 g/hr and 20 g/hr, respectively. The reaction was conducted with continuously discharging the reaction mixture which is the same amount as the charged one. From the results of the analyses by means of gas chromatography and $^{19}$F-NMR, it was found that after 20 hours of the reaction, the initial solvent R215cb was not present in the reaction mixture. The composition of the reaction products after 30 hours is shown in Table 15. 10.7 kg of the crude reaction products recovered since 20 hours later was purified by distillation to obtain 9.2 kg (yield: 86%) of dichloropentafluoropropane (R225).

EXAMPLE 22

The reaction was conducted in the same manner as in Example 21 except that zirconium fluoride chloride prepared in Preparation Example 2 was used instead of aluminum fluoride chloride. The composition of the reaction products after 30 hours of the reaction is shown in Table 15. 10.7 kg of a crude reaction products recovered since 20 hours later was purified by distillation to obtain 9.2 kg (yield: 86%) of dichloropentafluoropropane (R225).

EXAMPLE 23

The reaction was conducted in the same manner as in Example 21 except that 40 g/hr of titanium fluoride chloride prepared in Preparation Example 3 was supplied instead of aluminum fluoride chloride. The composition of the reaction products after 30 hours of the reaction is shown in Table 15. 10.7 kg of the crude reaction products recovered since 20 hours later was purified by distillation to obtain 9.2 kg (yield: 86%) of dichloropentafluoropropane (R225).

EXAMPLE 24

The reaction was conducted in the same manner as in Example 21 except that hafnium fluoride chloride was in Example 19 was employed instead of aluminum fluoride chloride. The composition of the reaction products after 30 hours of the reaction is shown in Table 15. 10.7 kg of the crude reaction products recovered since 20 hours later was purified by distillation to obtain 9.2 kg (yield: 86%) of dichloropentafluoropropane (R225).

EXAMPLE 25

The reaction was conducted in the same manner as in Example 21 except that 40 g/hr of tantalum fluoride chloride prepared in Preparation Example 4 was used instead of aluminum fluoride chloride. The composition of the reaction products after 30 hours is shown in Table 15. 10.7 kg of the crude reaction product recovered after 20 hours was purified by distillation to obtain 9 kg (yield: 84%) of dichloropentafluoropropane (R225).

TABLE 15

| Composition of the reaction solution (%) | Example Nos. | | | | |
|---|---|---|---|---|---|
| | 21 | 22 | 23 | 24 | 25 |
| R225ca | 58 | 40 | 39 | 40 | 60 |
| R225cb | 38 | 58 | 57 | 58 | 35 |
| Chloroform | 0 | 0 | 0 | 0 | 0 |
| R224ca | 2 | 1 | 3 | 1 | 3 |
| Others | 2 | 1 | 1 | 1 | 2 |

EXAMPLE 26

The reaction was conducted in the same manner as in Example 12 except that 0.1 kg of anhydrous aluminum chloride was used instead of aluminum fluoride chloride, whereby 10.7 kg of the crude reaction product was recovered. The results of the analyses by means of gas chromatography and NMR are shown in Table 16. The crude reaction product was purified by distillation to obtain 9.1 kg of R225 (dichloropentafluoropropane).

EXAMPLE 27

The reaction was conducted in the same manner as in Example 14 except that anhydrous zirconium(IV) chloride was used instead of zirconium(IV) fluoride chloride, whereby 10.7 kg of the crude reaction product was recovered. The results of the analyses by means of gas chromatography and NMR are shown in Table 16. The crude reaction product was purified by distillation to obtain 9 kg of R225 (dichloropentafluoropropane).

EXAMPLE 28

The reaction was conducted in the same manner as in Example 17 except that 0.1 kg of anhydrous titanium chloride was used instead of titanium fluoride chloride, whereby 10.5 kg of the crude reaction product was recovered. The results of the analyses by means of gas chromatography and NMR are shown in Table 16. The crude reaction product was purified by distillation to obtain 8.5 kg of R225 (dichloropentafluoropropane).

EXAMPLE 29

The reaction was conducted in the same manner as in Example 19 except that 0.1 kg of anhydrous hafnium tetrachloride was used instead of hafnium fluoride chloride, whereby 10.5 kg of a crude reaction products was recovered. The results of the analyses by means of gas chromatography and NMR are shown in Table 16. The crude reaction product was purified by distillation to obtain 8.9 kg of R225 (dichloropentafluoropropane).

EXAMPLE 30

The reaction was conducted in the same manner as in Example 16 except that 0.1 kg of anhydrous tantalum pentachloride was used instead of tantalum fluoride chloride, whereby 9 kg of the crude reaction product was recovered. The results of the analyses by means of gas chromatography and NMR are shown in Table 16. The crude reaction product was purified by distillation to obtain 7.5 kg of R225 (dichloropentafluoropropane).

TABLE 16

| Composition of the reaction solution (%) | Example Nos. | | | | |
|---|---|---|---|---|---|
| | 26 | 27 | 28 | 29 | 30 |
| R225ca | 71 | 58 | 59 | 59 | 64 |
| R225cb | 22 | 40 | 37 | 38 | 22 |
| Chloroform | 0.5 | 0.5 | 1 | 0.5 | 2 |
| R224ca | 2 | 1 | 2.5 | 1.5 | 8 |
| Others | 4.5 | 0.5 | 0.5 | 1 | 4 |

EXAMPLE 31

The reaction was conducted in the same manner as in Example 12 except that 3 kg (12.6 mol) of R215cb ($CF_3CF_2CCl_3$) was used instead of R225ca as the solvent for reaction and anhydrous aluminum chloride was used, whereby 10.5 kg of the crude reaction product was recovered. The results of the analyses by means of gas chromatography and $^{19}$F-NMR are shown in Table 17.

TABLE 17

| Composition of the reaction solution | | Molar ratio (%) |
|---|---|---|
| R225 | | |
| $CF_3CF_2CHCl_2$ | (R225ca) | 45 |
| $CClF_2CF_2CHClF$ | (R225cb) | 23 |
| R224b | | |
| $CClF_2CF_2CHCl_2$ | (R224ca) | 2 |
| $CHCl_3$ | (R20) | 0 |
| R215 | | |
| $CF_3CF_2CCl_3$ | (R215cb) | 24 |
| Other components | | 6 |

The crude reaction solution was purified by distillation to obtain 6.6 kg (yield: 84%) of R225 (dichloropentafluoropropane).

EXAMPLE 32

Into a 10 l Hastelloy C autoclave, 0.2 kg (1.5 mol) of anhydrous aluminum chloride was charged, and the autoclave was deaerated under reduced pressure. Then, autoclave was cooled to −10° C., and 5 kg (48.6 mol) of R21 ($CHCl_2F$) was added thereto. Then, while maintaining the reaction temperature within a range of from 0° to 5° C., tetrafluoroethylene was continuously added at the rate of 800 g/hr. The upper limit of the reaction pressure was 5 kg/cm$^2$, and the reaction was continued while purging the gas as the case required. Five hours later, the reaction temperature was raised to 20° C., and the reaction was continued with further supply of tetrafluoroethylene. When chloroform in the system was consumed, the reaction was stopped, and the pressure was returned to normal pressure. Then, the reaction solution was subjected to filtration, whereby 7.8 kg of the crude reaction product was recovered. The results of the analyses by means of gas chromatography and $^{19}$F-NMR are shown in Table 18.

TABLE 18

| Composition of the reaction solution | | Molar ratio (%) |
|---|---|---|
| R225 | | |
| $CF_3CF_2CHCl_2$ | (R225ca) | 37 |
| $CClF_2CF_2CHClF$ | (R225cb) | 10 |

TABLE 18-continued

| Composition of the reaction solution | | Molar ratio (%) |
|---|---|---|
| R224 | | |
| $CClF_2CF_2CHCl_2$ | (R224ca) | 36 |
| Other components | | 17 |

The crude reaction product was purified by distillation to obtain 3.5 kg (yield: 35%) of R225 (dichloropentafluoropropane).

EXAMPLE 33

A 10 l Hastelloy C autoclave was deaerated under reduced pressure. Then, 10 kg of R215cb ($Cf_3CF_2CCl_3$) was charged as the initial solvent.

The autoclave was cooled to −15° C. Then, while maintaining the reaction temperature within a range of from −10° C. to −5° C., tetrafluoroethylene, R21 and aluminum chloride were continuously added at the rates of 11300 g/hr, 1030 g/hr and 20 g/hr (1.5 mol% relative to R21, same applied hereinafter), respectively. The reaction was conducted with continuously withdrawing the reaction mixture which is the same amount as the charged one. From the results of the analyses by means of gas chromatography and $^{19}$F-NMR, it was found that after 20 hours of the reaction, the initial solvent R215cb was not present in the reaction mixture. The composition of the reaction solution at that time is shown in Table 19.

TABLE 19

| Composition of the reaction solution | | Molar ratio (%) |
|---|---|---|
| R225 | | |
| $CF_3CF_2CHCl_2$ | (R225ca) | 57 |
| $CClF_2CF_2CHClF$ | (R225cb) | 37 |
| R224 | | |
| $CClF_2CF_2CHCl_2$ | (R224ca) | 3 |
| $CHCl_3$ | (R20) | 0 |
| Other components | | 3 |

The reaction mixture which is the same amount as the charged one was continuously withdrawn, and 10.7 kg of the crude reaction product thereby obtained was purified by distillation to obtain 9.1 kg (yield: 85%) of R225 (dichloropentafluoropropane).

EXAMPLE 34

The reaction was conducted in the same manner as in Example 33 except that the supplying rates of tetrafluoroethylene, R21 and aluminum chloride were doubled by twice, whereby 10.5 kg of the crude reaction product was recovered. The results of the analyses by means of gas chromatography and $^{19}$F-NMR are shown in Table 20.

TABLE 20

| Composition of the reaction solution | | Molar ratio (%) |
|---|---|---|
| R225 | | |
| $CF_3CF_2CHCl_2$ | (R225ca) | 55 |
| $CClF_2CF_2CHClF$ | (R225cb) | 36 |
| R224 | | |
| $CClF_2CF_2CHCl_2$ | (R224ca) | 5 |
| $CHCl_3$ | (R20) | 0 |
| Other components | | 4 |

The crude reaction product was purified by distillation to obtain 8.8 kg (yield: 84%) of R225 (dichloropentafluoropropane).

EXAMPLE 35

The reaction was conduced in the same manner as in Example 33 except that the supplying rate of aluminum chloride was changed to 67 g/hr (5.5 mol%), whereby 9.8 kg of the crude reaction product was recovered. The results of the analyses by means of gas chromatography and $^{19}$F-NMR are shown in Table 21.

TABLE 21

| Composition of the reaction solution | | Molar ratio (%) |
|---|---|---|
| R225 | | |
| CF$_3$CF$_2$CHCl$_2$ | (R225ca) | 53 |
| CClF$_2$CF$_2$CHClF | (R225cb) | 37 |
| R224 | | |
| CClF$_2$CF$_2$CHCl$_2$ | (R224ca) | 5 |
| CHCl$_3$ | (R20) | 1 |
| Other components | | 4 |

The crude reaction product was purified by distillation to obtain 8.0 kg (yield: 82%) of R225 (dichloropentafluoropropane).

EXAMPLE 36

The reaction was conducted in the same manner as in Example 26 except that the reaction temperature was changed in the range of 0° to 5° C., whereby 8.5 kg of the crude reaction product was recovered. The results of the analyses by means of gas chromatography and $^{19}$F-NMR are shown in Table 22.

TABLE 22

| Composition of the reaction solution | | Molar ratio (%) |
|---|---|---|
| R225 | | |
| CF$_3$CF$_2$CHCl$_2$ | (R225ca) | 52 |
| CClF$_2$CF$_2$CHClF | (R225cb) | 36 |
| R224 | | |
| CClF$_2$CF$_2$CHCl$_2$ | (R224ca) | 5 |
| CHCl$_3$ | (R20) | 0 |
| Other components | | 7 |

The crude reaction product was purified by distillation to obtain 6.8 kg (yield: 80%) of R225 (dichloropentafluoropropane).

EXAMPLE 37

The reaction was conducted in the same manner as in Example 33 except that the catalyst was changed to zirconium(IV) chloride, and the supplying rate of the catalyst was changed to 20 g/hr (0.9 mol%), whereby 11 kg of the crude reaction solution was recovered. The results of the analyses by means of gas chromatography and NMR are shown in Table 23.

TABLE 23

| Composition of the reaction solution | Molar ratio (%) |
|---|---|
| R225ca | 39 |
| R225cb | 58 |
| Chloroform | 0 |
| R224 (CClF$_2$CF$_2$CHCl$_2$) | 2 |
| Other components | 1 |

The crude reaction solution was purified by distillation to obtain 9.5 kg (yield: 86%) of R225 (dichloropentafluoropropane).

EXAMPLE 38

The reaction was conducted in the same manner as in Example 33 except that the catalyst was changed to titanium tetrachloride, and the supplying rate of the catalyst was changed to 20 g/hr (1.1 mol%), whereby 11 kg of the crude reaction solution was recovered. The results of the analyses by means of gas chromatography and NMR are shown in Table 24.

TABLE 24

| Composition of the reaction solution | Molar ratio (%) |
|---|---|
| R225ca | 38 |
| R225cb | 56 |
| Chloroform | 0 |
| R224ca | 4 |
| Other components | 2 |

The crude reaction solution was purified by distillation to obtain 9.2 kg (yield: 84%) of R225 (dichloropentafluoropropane).

EXAMPLE 39

The reaction was conducted in the same manner as in Example 33 except that the catalyst was changed to zirconium dichloride difluoride, and the supplying rate of the catalyst was changed to 20 g/hr (1 mol%), whereby 11 kg of the crude reaction product was recovered. The results of the analyses by means of gas chromatography and NMR are shown in Table 25.

TABLE 25

| Composition of the reaction solution | Molar ratio (%) |
|---|---|
| R225ca | 39 |
| R225cb | 58 |
| Chloroform | 0 |
| R224ca (CClF$_2$CF$_2$CHCl$_2$) | 2 |
| Other components | 1 |

The crude reaction product was purified by distillation to obtain 9.5 kg (yield: 86%) of R225 (dichloropentafluoropropane).

EXAMPLE 40

The reaction was conducted in the same manner as in Example 33 except that the catalyst was changed to titanium chloride difluoride, and the supplying rate of the catalyst was changed to 20 g/hr (1.3 mol%), whereby 11 kg of the crude reaction solution was recovered. The results of the analyses by means of gas chromatography and NMR are shown in Table 26.

TABLE 26

| Composition of the reaction solution | Molar ratio (%) |
|---|---|
| R225ca | 38 |
| R225cb | 56 |
| Chloroform | 0 |
| R224ca | 4 |
| Other components | 2 |

The crude reaction solution was purified by distillation to obtain 9.2 kg (yield: 84%) of R225 (dichloropentafluoropropane).

EXAMPLE 41

The reaction was conducted in the same manner as in Example 33 except that the catalyst was changed to gallium trichloride, and the supplying rate of the catalyst was changed to 20 g/hr (1.1 mol%), whereby 11 kg of a crude reaction solution was recovered. The results of the analyses by means of gas chromatography and NMR are shown in Table 27.

TABLE 27

| Composition of the reaction solution | Molar ratio (%) |
|---|---|
| R225ca | 40 |
| R225cb | 50 |
| Chloroform | 1 |
| R224ca | 7 |
| Other components | 2 |

The crude reaction solution was purified by distillation to obtain 9 kg (yield: 81%) of R225 (dichloropentafluoropropane).

EXAMPLE 42

The reaction was conducted in the same manner as in Example 33 except that the catalyst was changed to hafnium tetrachloride, and the supplying rate of the catalyst was changed to 20 g/hr (0.6 mol%), whereby 11 kg of the crude reaction solution was recovered. The results of the analyses by means of gas chromatography and NMR are shown in Table 28.

TABLE 28

| Composition of the reaction solution | Molar ratio (%) |
|---|---|
| R225ca | 38 |
| R225cb | 57 |
| Chloroform | 0 |
| R224ca | 3 |
| Other components | 2 |

The crude reaction solution was purified by distillation to obtain 9.5 kg (yield: 86%) of R225 (dichloropentafluoropropane).

As shown by the Examples, according to the present invention, dichloropentafluoropropane (R225), a high-purity product of which used to be hardly available, can be produced in good yield.

We claim:

1. A method for producing dichloropentafluoropropane, which comprises reaction dichlorofluoromethane with tetrafluoroethylene in the presence of a Lewis acid catalyst for addition reaction to obtain dichloropentafluoropropane, wherein said Lewis acid is a fluoride of the formula:

$$MX_\alpha F_\beta$$

wherein M is one of atoms selected from Group IVa, Group Va and Group IIIb, or a mixture of such atoms, X is one of Cl, Br and I atoms, or a mixture of such atoms, $\alpha$ is a real number of $0<\alpha<5$, and $\beta$ is a real number of $0<\beta\leq3.5$ in the case of Group IVa, a real number of $0<\beta\leq4.5$ in the case of Group Va, and a real number of $0<\beta\leq2.5$ in the case of Group IIIb, provided that $\alpha+\beta$ is an integer of from 3 to 5.

2. The method according to claim 1, wherein the fluoride is a compound obtained by fluorinating a halogen compound of the formula:

$$MX_\alpha$$

wherein M is one of atoms selected from Group IVa, Group Va and Group IIIb, or a mixture of such atoms, X is one of Cl, Br, and I atoms, or a mixture of such atoms, and $\alpha$ is $\alpha=4$ in the case of Group IVa, $\alpha=5$ in the case of Group Va, and $\alpha=3$ in the case of Group IIIb, with a fluorinating agent.

3. The method according to claim 2, wherein chlorofluorocarbon or hydrochlorofluorocarbon is used as the fluorinating agent.

* * * * *